(12) United States Patent
MacFarland et al.

(10) Patent No.: US 11,035,798 B2
(45) Date of Patent: Jun. 15, 2021

(54) FLUORESCENT MEASUREMENT OF FILMING AMINES

(71) Applicant: Hach Company, Loveland, CO (US)

(72) Inventors: Darren Kent MacFarland, Windsor, CO (US); Rachel Nicole Seals, Longmont, CO (US)

(73) Assignee: HACH COMPANY, Loveland, CO (US)

( * ) Notice: Subject to any disclaimer, the term of this patent is extended or adjusted under 35 U.S.C. 154(b) by 14 days.

(21) Appl. No.: 16/512,054

(22) Filed: Jul. 15, 2019

(65) Prior Publication Data

US 2021/0018442 A1 Jan. 21, 2021

(51) Int. Cl.
| | | |
|---|---|---|
| *G01N 21/77* | (2006.01) | |
| *G01N 31/22* | (2006.01) | |
| *G01N 33/18* | (2006.01) | |
| *G01N 21/76* | (2006.01) | |
| *C23F 11/00* | (2006.01) | |
| *C23F 11/14* | (2006.01) | |

(52) U.S. Cl.
CPC ............. *G01N 21/76* (2013.01); *G01N 21/77* (2013.01); *G01N 31/22* (2013.01); *G01N 33/18* (2013.01); *C23F 11/00* (2013.01); *C23F 11/141* (2013.01)

(58) Field of Classification Search
CPC ........ G01N 21/76; G01N 21/77; G01N 33/18; G01N 31/22; C23F 11/00; C23F 11/141
See application file for complete search history.

(56) References Cited

U.S. PATENT DOCUMENTS

| | | | | |
|---|---|---|---|---|
| 2013/0102086 A1* | 4/2013 | Pellet | ...................... | G01N 21/78 436/169 |
| 2015/0260702 A1* | 9/2015 | Richardson | ............. | C02F 1/008 436/172 |

FOREIGN PATENT DOCUMENTS

| | | | | | |
|---|---|---|---|---|---|
| KR | 20160039017 A | * | 4/2016 | ............. | G01N 31/22 |
| WO | WO-2014166542 A1 | * | 10/2014 | ............. | G01N 31/22 |
| WO | WO-2019023699 A1 | * | 1/2019 | ............. | G01N 33/18 |

OTHER PUBLICATIONS

Translation of Han, Min Su, Apr. 8, 2016, KR-20160039017-A (Year: 2016).*
Ying Zhou et al., "Recent progress in fluorescent and colorimetric chemosensors for detection of amino acids", Chemical Society Reviews, 2012, 42 pages, Royal Society of Chemistry.
Jessica L. Klockow et al., "Fluorescent Sensors for Amines", Dec. 2016, 22 pages, ResearchGate.

* cited by examiner

*Primary Examiner* — Jill A Warden
*Assistant Examiner* — Henry H Nguyen
(74) *Attorney, Agent, or Firm* — Ference & Associates LLC (57) ABSTRACT

An embodiment provides a method for measuring amines in a solution, including: preparing an indicator-metal complex, wherein the indicator-metal complex comprises an indicator and a metal; introducing the indicator-metal complex to a solution, wherein the solution contains an amount of amine, wherein the amine activates the indicator-metal complex causing a change in fluorescence intensity of the indicator-metal complex; and measuring the amount of amine in the solution by measuring the change in fluorescence intensity of the indicator-metal complex.

18 Claims, 5 Drawing Sheets

FLUORESCENT MEASUREMENT OF FILMING AMINES

BACKGROUND

This application relates generally to measuring filming amines in aqueous or liquid samples, and, more particularly, to the measurement of filming amines using fluorescent techniques.

Many processes require the use of steam cycle chemistry. The steam cycle may be a circulation of feed water and condensate systems. The steam cycle may require maintenance. One maintenance item may be ensuring that the steam cycle system does not become clogged, damaged, corroded, or the like. One method to prevent corrosion inside the steam cycle system is to use amines in the solution. The amines may prevent corrosion inside the piping, tanks, heating chambers, or the like of the steam cycle by creating a protective film. A way to measure the amount of amine in the steam cycle system is necessary.

BRIEF SUMMARY

In summary, one embodiment provides a method for measuring amines in a solution, comprising: preparing an indicator-metal complex, wherein the indicator-metal complex comprises an indicator and a metal; introducing the indicator-metal complex to a solution, wherein the solution contains an amount of amine, wherein the amine activates the indicator-metal complex causing a change in fluorescence intensity of the indicator-metal complex; and measuring the amount of amine in the solution by measuring the change in fluorescence intensity of the indicator-metal complex.

Another embodiment provides a measurement device for measuring amines in a solution, comprising: a processor; and a memory storing instructions executable by the processor to: prepare an indicator-metal complex, wherein the indicator-metal complex comprises an indicator and a metal; introduce the indicator-metal complex to a solution, wherein the solution contains an amount of amine, wherein the amine activates the indicator-metal complex causing a change in fluorescence intensity of the indicator-metal complex; and measure the amount of amine in the solution by measuring the fluorescence intensity of the indicator-metal complex.

A further embodiment provides a method for measuring amines in a solution, comprising: preparing an indicator-metal complex, wherein the indicator-metal complex comprises a calcein blue derivative and a metal; introducing the indicator-metal complex to a solution, wherein the solution contains an amount of amine, wherein the amine activates the indicator-metal complex causing a change in fluorescence intensity of the indicator-metal complex, wherein the solution comprises a fluid for a steam cycle system; and measuring the amount of amine in the solution by measuring the fluorescence intensity of the indicator-metal complex, wherein the indicator-metal complex is weakly fluorescent and wherein the amine activates the indicator-metal complex by removing the metal from the indicator-metal complex, thereby causing the change in fluorescence intensity.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example Conventional steam cycle systems suffer from many disadvantages. For example, water may be heated in a heat transfer unit then and piped to a condenser for cooling. Water in a closed loop system may contain contaminants such as impurities, rust, or the like. These contaminants may degrade the ability of the steam cycle system to work efficiently. For example, impurities (like dissolved gases) in the steam cycle water may cause thinning of the metal within the system which may lead to pipe failure. Filming amines may be used to prevent this type of corrosion during normal operation and/or layup of the steam cycle chemistry system.

One method to prevent corrosion inside a steam cycle system is the use of filming amines. Filming amines may be used in both closed and open loop steam cycle chemistry systems. Filming amines may be biodegradable, and may have no hazardous materials. These characteristics make filming amines a good choice in steam cycle systems. Additionally, filming amines may have an affinity for metal surfaces. The filming amines may have a hydrophobic tail that may orient toward the steam cycle fluid or steam. Thus, filming amines provide a barrier to the steam cycle system preventing corrosion, or the like.

However, the use of filming amines does involve time, energy, and expense to a facility. For example, the amount of filming amines in a steam cycle system may be monitored. Monitoring may require the facility to send personnel out to areas of the steam cycle system to collect a system sample. The sample may be from condensate of the steam cycle system. The samples may need to be returned to a lab for analysis. This represents both time and money to a facility. Also, filming amines may be a significant cost to a facility. An amount of filming amines required for a steam cycle system may depend on the type of filming amine used and/or whether the filming amines are used for continuous operation, layup, or a combination thereof. Filling and/or replenishing a system may be a significant cost to a facility. What is needed is a method and system to measure the amount of filming amines in a steam cycle system.

Accordingly, an embodiment provides a system and method for measuring filming amines using an indicator-metal complex. The indicator-metal complex comprises an indicator and a metal. The indicator may be a calcein blue derivative, methyl calcein blue, or calcein blue. The metal may be copper (II), cobalt(II), nickel (II), or iron (II). The indicator-metal complex may be introduced into a solution containing amines. The amine may cause a change in the fluorescence intensity of the indicator-metal complex. The change in fluorescence intensity may be correlated to an amount of amine in solution. Additionally or alternatively, the intensity of the fluorescence may correlate to a specific type of amine. The indicator-metal complex may detect amines such as ethanolamine, diethylenetriamine, Cetamine® (Kurita America, Inc.), Helamin® (Helamin, France), Steamate® (SUEZ Trevose Pa.), DPL-674® (Solenis, Wilmington Del.), or the like. In an embodiment, the indicator-metal complex may be weakly fluorescent. The amine may activate the indicator-metal complex by removing the metal from the indicator-metal complex, thereby causing the change in fluorescence intensity. In an embodiment, the indicator-metal complex is weakly fluorescent and wherein the change in fluorescence intensity is caused by the amine removing the metal from the indicator-metal complex and releasing the indicator. The method and system described herein may be used to quantify an amount of filming amine in a steam cycle system using a change in fluorescent intensity of an indicator-metal complex.

The illustrated example embodiments will be best understood by reference to the figures. The following description is intended only by way of example, and simply illustrates certain example embodiments.

Figure 1:
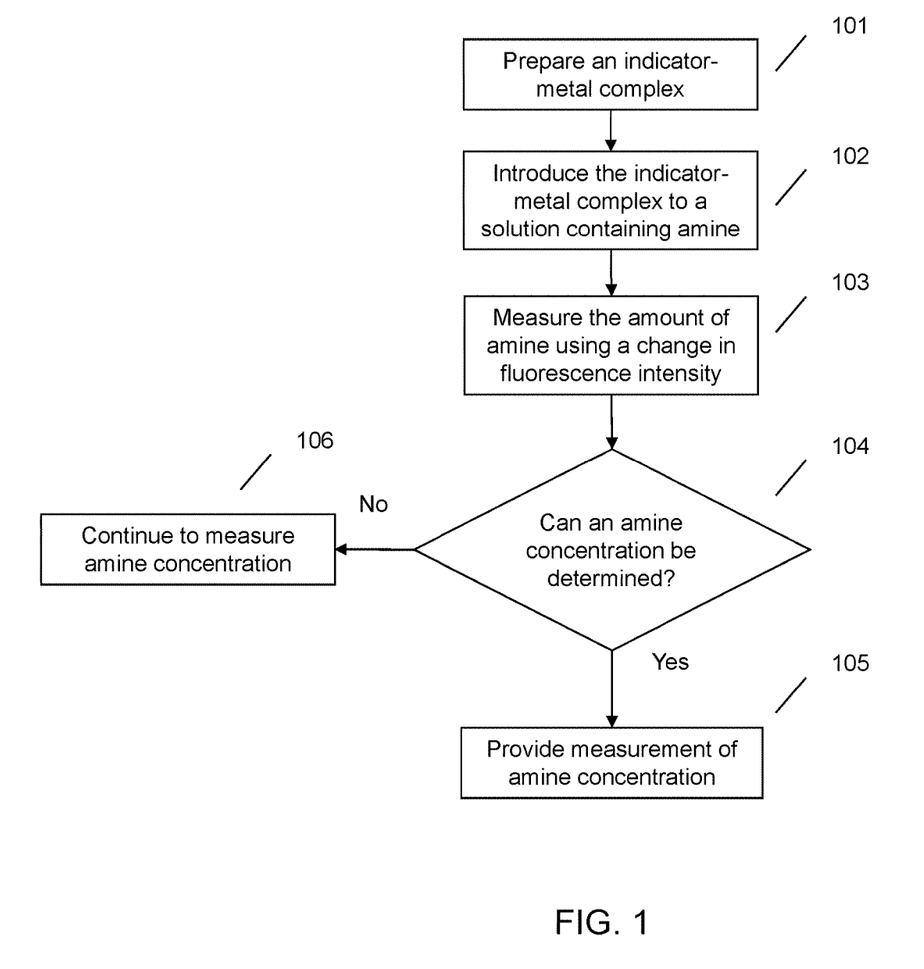
FIG. 1 illustrates a flow diagram of an example filming amine measuring system.

Referring to FIG. 1, an example system and method for detection of amine in solution is illustrated. In an embodiment, an indicator-metal complex may be prepared. The indicator-metal complex indicator may be introduced to a solution containing amine. In an embodiment, the indicator-metal complex in the presence of amine may cause a change in fluorescence intensity of the indicator-metal complex. The change of fluorescence intensity may be correlated to a concentration of amine in the solution.

Figure 2:
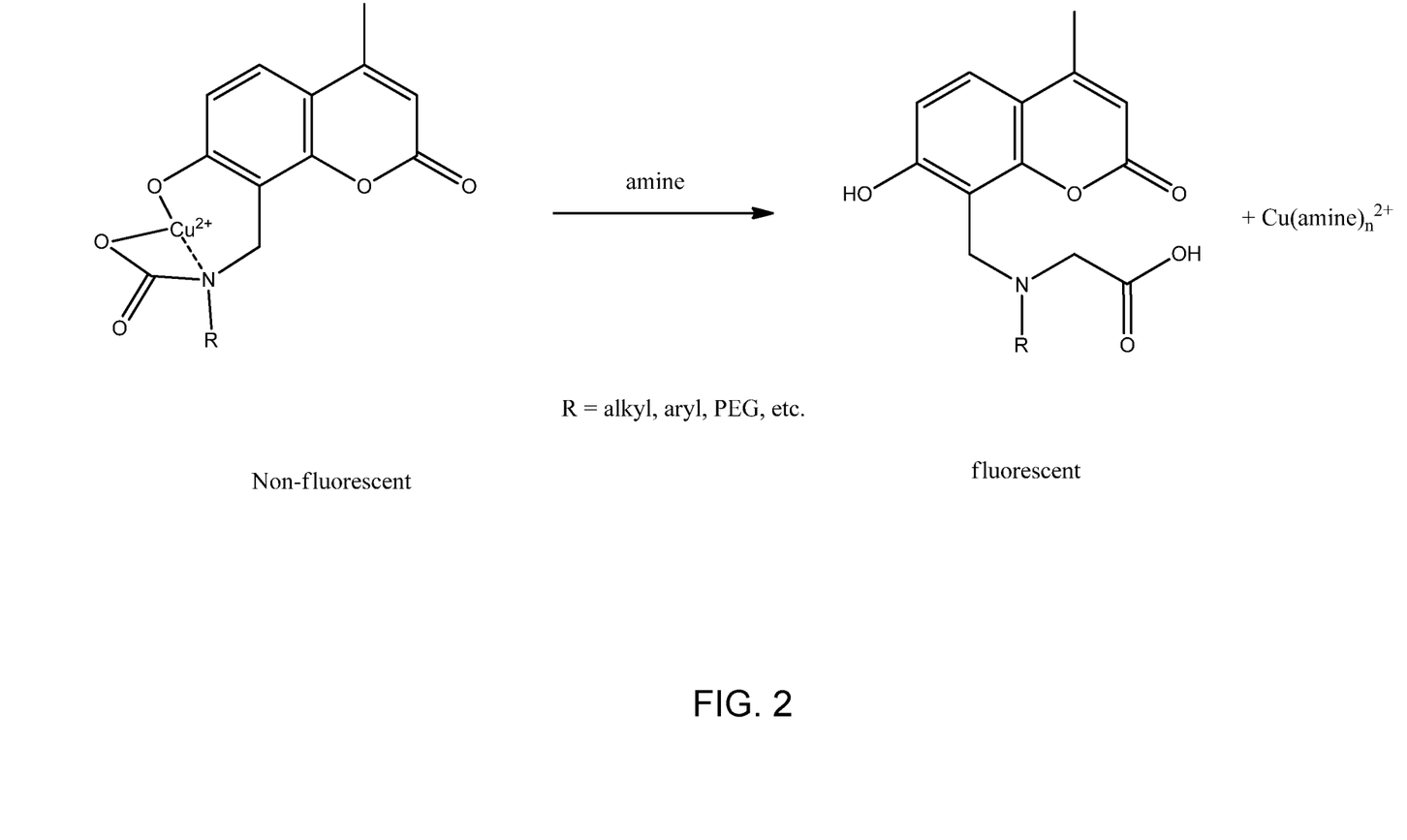
FIG. 2 illustrates a chemical equation of an example fluorescent indicator for detection of filming amines.

At 101, in an embodiment, an indicator-metal complex may be prepared. The indicator-metal complex may contain an indicator and a metal. The indicator may be a calcein blue derivative or calcein blue. The metal may be copper (II), cobalt(II), nickel (II), or iron (II). Referring to FIG. 2, an example reaction of the indicator-metal complex is illustrated. In an embodiment, the indicator-metal complex may detect amine in a solution. The indicator-metal complex may undergo a structural change in the presence or absence of amine. For example, in the absence of amine, the copper of the indicator-metal complex may have a bond with oxygen and nitrogen. In the absence of amine, the indicator-metal complex may be weakly fluorescent. In the presence of amine, the bonds may be broken releasing the copper. In the presence of amines, the indicator-metal complex may be fluorescent. Therefore, the indicator may undergo a change in fluorescence intensity based upon an amount of amine in a solution.

At 102, in an embodiment, the indicator-metal complex may be introduced into a solution. The solution may contain amine or a plurality of amines. The solution may be an aqueous sample which may include a sample from a facility steam cycle system, natural body of water, a holding tank, a processing tank, a pipe, or the like. The solution may be in a continuous flow, a standing volume of liquid, or any combination thereof. In one embodiment, the solution may be introduced to the indicator-metal complex, for example, a test chamber of the measurement device. In an embodiment, the measurement device may be a hand held device. Alternatively, the measurement device may be a larger bench top device. Introduction of the solution into the measurement device may include placing or introducing the solution into a test chamber manually by a user or using a mechanical means, for example, gravity flow, a pump, pressure, fluid flow, or the like. For example, a water sample for amine testing may be introduced to a measurement or test chamber using a pump. In an embodiment, valves or the like may control the influx and efflux of the solution into or out of the one or more chambers, if present. Alternatively, the measurement device may be connected directly to a steam cycle system. For example, a change in fluorescence intensity may be measured in a sample of solution flowing through the measurement device from a steam cycle system.

Additionally or alternatively, the measurement device may be present or introduced in a volume of the solution. The measurement device is then exposed to the volume of solution where it may perform measurements. The system may be a flow-through system in which a solution and/or reagents are automatically mixed and measured. Once the sample is in contact with the measurement system, the system may measure the amine of the sample, as discussed in further detail herein. In an embodiment, the measurement device may include one or more chambers in which the one or more method steps may be performed.

Figure 3:
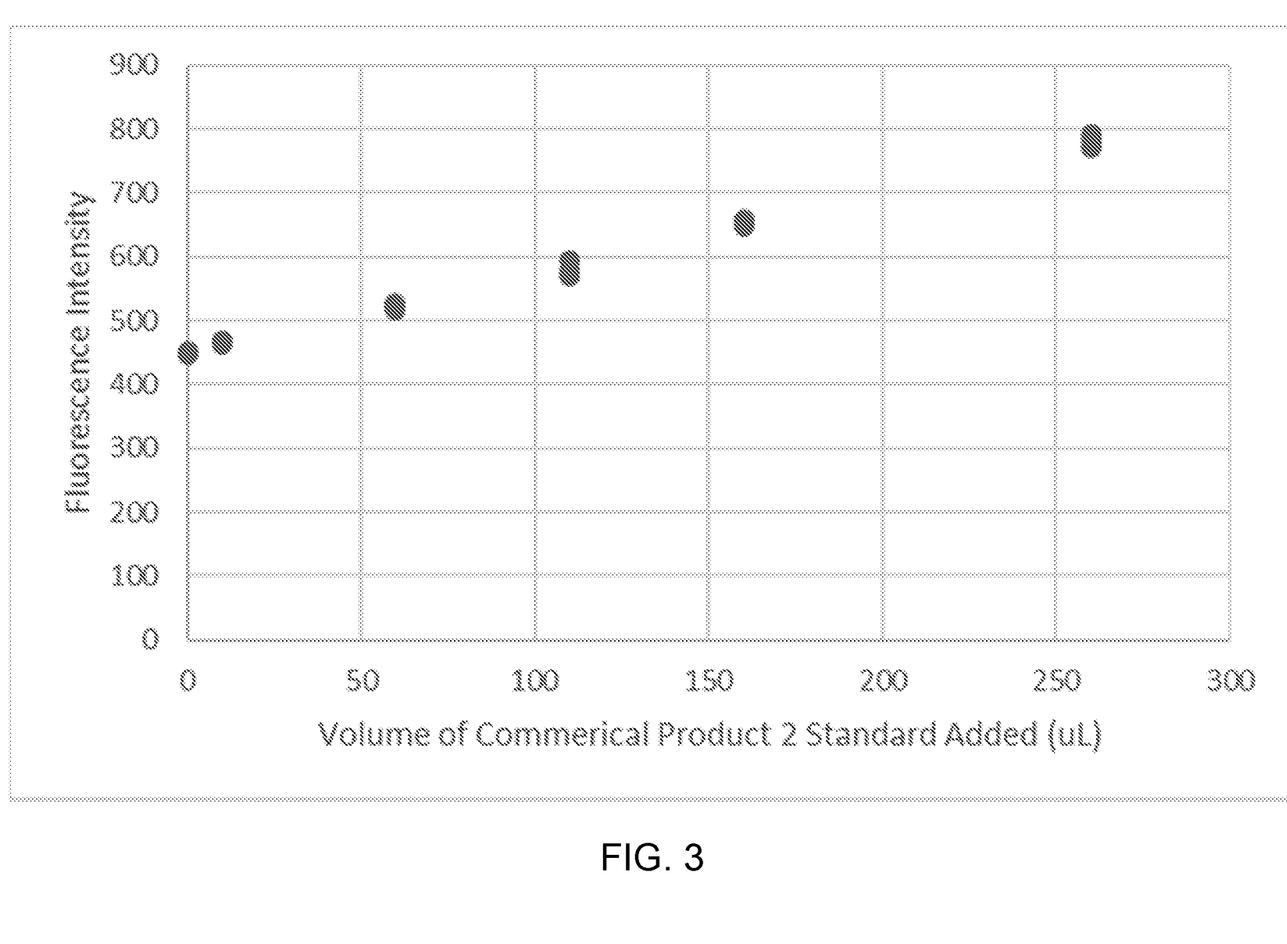
FIG. 3 illustrates an example fluorescence intensity measurement of an amine sensitive indicator.

At 103, in an embodiment, the system and method may measure an amount of amine in a solution using a change in the fluorescent intensity. In an embodiment, the indicator-metal complex may be weakly fluorescent in the absence of amine and fluorescent in the presence of amine, as described above and in FIG. 2. Referring to FIG. 3, an example indicator-metal complex is illustrated. For example, an indicator-metal complex of calcein blue and copper in the presence of an amine illustrates an increase of fluorescence intensity based upon amine concentration. In an embodiment, a concentration of about 0.5 to 10 µM of calcein blue, calcein blue derivative, or methyl calcein blue may be used. In an embodiment, an emission wavelength of 445 nm may be used. A borate buffer may be used in the measurement process. In an embodiment, amine may be measured in the 0.05-2.5 ppm range. However, reaction parameters may be adjusted for optimal results, and values are purely illustrative. In an embodiment, the indicator-metal complex may detect amine such as, but not limited to: ethanolamine, diethylenetriamine, Cetamine, and Helamin.

Figure 4:
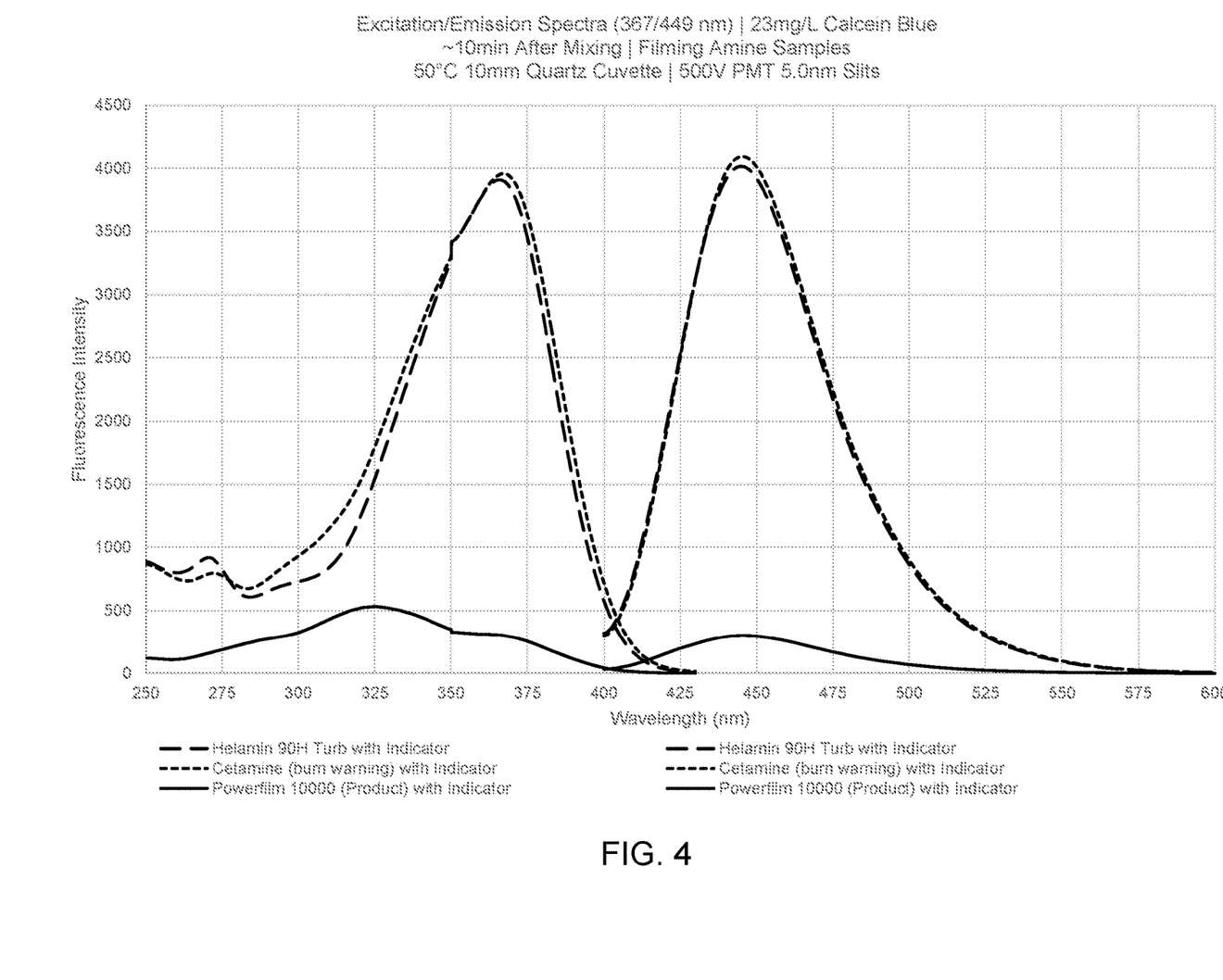
FIG. 4 illustrates an example fluorescence intensity measurement of an amine sensitive indicator in the presence of filming amines.

At 104, in an embodiment, the system and method may determine if an amount of amine in solution may be measured. In an embodiment, the presence of amine in an aqueous solution may cause an increase in fluorescence intensity of the indicator-metal complex. Examples of different commercially available filming amines and associated excitation/emission spectra with the indicator-metal complex may be illustrated in FIG. 4. Therefore, the fluorescence intensity, of a solution containing an amount of amine may be correlated to the concentration of the amine in the aqueous solution. Fluorescence curves may be generated for a range of amine concentrations, for different indicator-metal complexes, for any different condition that may affect absorption or fluorescence values (e.g., temperature, sample content, turbidity, viscosity, measurement apparatus, aqueous sample chamber, etc.), or the like.

Alternatively or additionally, amine concentration measurement may be at periodic intervals set by the user or preprogrammed frequencies in the device. Measurement of amine by a device allows for real time data with very little human involvement in the measurement process. Cleaning of the fluorometric chamber may be required at an unspecified time interval. A programmed calibration curve may be entered into the device.

A chamber, vessel, cell, chamber, or the like may contain an aqueous sample, at least one indicator-metal complex, and associated reagents such as buffers and/or additives. The aqueous sample may be a solution from a steam cycle system containing amine. A device may contain one or more bottles of reagents which contain necessary reagents. The reagents contained in the one or more bottles may be pump fed or gravity fed. The flow of the reagents may be metered to ensure proper volume delivery to the measurement cell. The aqueous sample may be fed through a pressured inlet, a vessel, or the like. The aqueous sample may be introduced into the measurement chamber by a pump or gravity fed. The sampling device may be in series or parallel to an aqueous flow. The device may have a system to ensure proper mixing of the aqueous sample, indicator-metal complex, and related reagents.

The fluorescence intensity or amine concentration may be an output upon a device in the form of a display, printing, storage, audio, haptic feedback, or the like. Alternatively or additionally, the output may be sent to another device through wired, wireless, fiber optic, Bluetooth®, near field communication, or the like. An embodiment may use an alarm to warn of a measurement or concentration outside acceptable levels. An embodiment may use a system to shut down water output or shunt water from sources with unacceptable levels. For example, an analyte measuring device may use a relay coupled to an electrically actuated valve, or the like.

At 106, in an embodiment, if a concentration of amine cannot be determined, the system may continue to measure amine. Additionally or alternatively, the system may output an alarm, log an event, or the like.

At 105, if a concentration of amine can be determined, the system may provide a measurement of the amount of amine in solution. The system may connect to a communication network. The system may alert a user or a network. This alert may occur whether an amine measurement is determined or not. An alert may be in a form of audio, visual, data, storing the data to a memory device, sending the output through a connected or wireless system, printing the output or the like. The system may log information such as the measurement location, a corrective action, geographical location, time, date, number of measurement cycles, or the like. The alert or log may be automated, meaning the system may automatically output whether a correction was required or not. The system may also have associated alarms, limits, or predetermined thresholds. For example, if an amine concentration reaches a threshold. Alarms or logs may be analyzed in real-time, stored for later use, or any combination thereof.

The various embodiments described herein thus represent a technical improvement to conventional amine measurement techniques. Using the techniques as described herein, an embodiment may use an indicator-metal complex to measure an amount of amine in solution. This is in contrast to taking sample throughout a steam cycle system for lab analysis. The methods and system described herein provide a faster and cost effective method for measuring amine in an aqueous or liquid solution.

Figure 5:
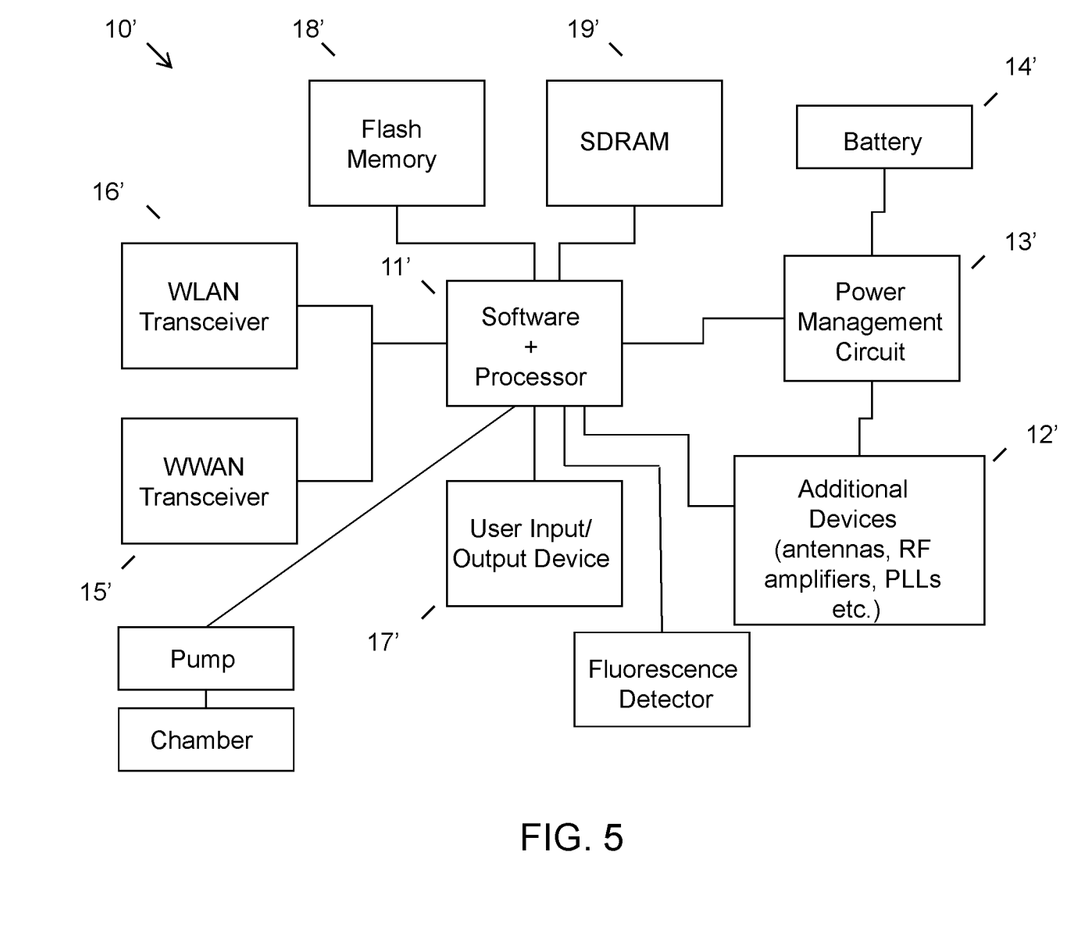
FIG. 5 illustrates an example of computer circuitry.

While various other circuits, circuitry or components may be utilized in information handling devices, with regard to an instrument for measurement of amines according to any one of the various embodiments described herein, an example is illustrated in FIG. 5. Device circuitry 10' may include a measurement system on a chip design found, for example, a particular computing platform (e.g., mobile computing, desktop computing, etc.) Software and processor(s) are combined in a single chip 11'. Processors comprise internal arithmetic units, registers, cache memory, busses, I/O ports, etc., as is well known in the art. Internal busses and the like depend on different vendors, but essentially all the peripheral devices (12') may attach to a single chip 11'. The circuitry 10' combines the processor, memory control, and I/O controller hub all into a single chip 11'. Also, systems 10' of this type do not typically use SATA or PCI or LPC. Common interfaces, for example, include SDIO and I2C.

There are power management chip(s) 13', e.g., a battery management unit, BMU, which manage power as supplied, for example, via a rechargeable battery 14', which may be recharged by a connection to a power source (not shown). In at least one design, a single chip, such as 11', is used to supply BIOS like functionality and DRAM memory.

System 10' typically includes one or more of a WWAN transceiver 15' and a WLAN transceiver 16' for connecting to various networks, such as telecommunications networks and wireless Internet devices, e.g., access points. Additionally, devices 12' are commonly included, e.g., a transmit and receive antenna, oscillators, PLLs, etc. System 10' includes input/output devices 17' for data input and display/rendering (e.g., a computing location located away from the single beam system that is easily accessible by a user). System 10' also typically includes various memory devices, for example flash memory 18' and SDRAM 19'.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment to perform measurement of amines of an aqueous sample.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring amines in a solution, comprising:
preparing, within at least one chamber, an indicator-metal complex, wherein the indicator-metal complex comprises introducing and combining an indicator and a metal into and within the at least one chamber;
introducing, using a pump, the indicator-metal complex to the solution, wherein the solution contains an amount of the amines, wherein the amines activate the indicator-metal complex causing a change in fluorescence intensity of the indicator-metal complex; and
measuring, using a fluorescence detector, the amount of the amines in the solution by measuring, using the fluorescence detector, the change in fluorescence intensity of the indicator-metal complex, wherein the amount of amines comprise a non-aromatic amine with a hydrophobic tail.

2. The method of claim 1, wherein the indicator comprises a calcein blue derivative.

3. The method of claim 1, wherein the metal is selected from the group consisting of: copper (II), cobalt (II), nickel (II), and iron (II).

4. The method of claim 1, wherein the solution comprises a fluid in a steam cycle system.

5. The method of claim 1, wherein the amines comprise a filming agent that reduces degradation of a steam cycle system.

6. The method of claim 1, wherein the amines comprise at least ethanolamine.

7. The method of claim 1, wherein the solution further comprises at least one of: a borate buffer and a carbonate buffer.

8. The method of claim 1, wherein the indicator-metal complex is fluorescent and wherein the amines activate the indicator-metal complex by removing the metal from the indicator-metal complex, thereby causing the change in fluorescence intensity.

9. The method of claim 1, wherein the fluorescence intensity is correlated to the amount of the amines in the solution.

10. A measurement device that measures amines in a solution, comprising:
at least one chamber;
a pump;
a fluorescence detector;
a processor; and
a storage device that stores code, the code being executable by the processor and configured to:
prepare, within the at least one chamber, an indicator-metal complex, wherein to prepare the indicator-metal complex comprises introducing and combining an indicator and a metal into and within the at least one chamber;
introduce, using the pump, the indicator-metal complex to the solution, wherein the solution contains an amount of the amines, wherein the amines activate the indicator-metal complex causing a change in fluorescence intensity of the indicator-metal complex; and
measure, using the fluorescence detector, the amount of the amines in the solution, using the fluorescence detector, by measuring the fluorescence intensity of the indicator-metal complex, wherein the amount of amines comprise a non-aromatic amine with a hydrophobic tail.

11. The device of claim 10, wherein the indicator comprises a calcein blue derivative.

12. The device of claim 10, wherein the metal is selected from the group consisting of: copper (II), cobalt (II), nickel (II), and iron (II).

13. The device of claim 10, wherein the solution comprises a fluid in a steam cycle system.

14. The device of claim 10, wherein the amines comprises a filming agent that reduces degradation of a steam cycle system.

15. The device of claim 10, wherein the amines comprise at least ethanolamine.

16. The device of claim 10, wherein the solution further comprises at least one of: a borate buffer and a carbonate buffer.

17. The device of claim 10, wherein the indicator-metal complex is fluorescent and wherein the amines activate the indicator-metal complex by removing the metal from the indicator-metal complex, thereby causing the change in fluorescence intensity.

18. A method for measuring amines in a solution, comprising:
    preparing, within at least one chamber, an indicator-metal complex, wherein the indicator-metal complex comprises introducing and combining a calcein blue derivative and a metal into and within the at least one chamber;
    introducing, using a pump, the indicator-metal complex to the solution, wherein the solution contains an amount of the amines, wherein the amine activates the indicator-metal complex causing a change in fluorescence intensity of the indicator-metal complex, wherein the solution comprises a fluid for a steam cycle system; and
    measuring, using a fluorescence detector, the amount of the amines in the solution by measuring, using the fluorescence detector, the fluorescence intensity of the indicator-metal complex, wherein the indicator-metal complex is fluorescent and wherein the amines activate the indicator-metal complex by removing the metal from the indicator-metal complex, thereby causing the change in fluorescence intensity, wherein the amount of amines comprise a non-aromatic amine with a hydrophobic tail.

* * * * *